US008101543B2

(12) United States Patent
Weerawarna

(10) Patent No.: US 8,101,543 B2
(45) Date of Patent: Jan. 24, 2012

(54) BIODEGRADABLE SUPERABSORBENT PARTICLES

(75) Inventor: S Ananda Weerawarna, Seattle, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 833 days.

(21) Appl. No.: 12/164,991

(22) Filed: Jun. 30, 2008

(65) Prior Publication Data

US 2009/0325799 A1  Dec. 31, 2009

(51) Int. Cl.
*B01J 20/00* (2006.01)
(52) U.S. Cl. ........................................ 502/404; 502/526
(58) Field of Classification Search .................. 502/400, 502/401, 404, 414, 415, 439, 514
See application file for complete search history.

(56) References Cited

U.S. PATENT DOCUMENTS

| | | |
|---|---|---|
| 3,645,836 A | 2/1972 | Torr |
| 4,028,290 A | 6/1977 | Reid |
| 4,128,692 A | 12/1978 | Reid |
| 4,143,163 A | 3/1979 | Hutchison et al. |
| 4,273,118 A | 6/1981 | Smith |
| 4,319,956 A | 3/1982 | Snyder et al. |
| 4,454,055 A | 6/1984 | Richman et al. |
| 4,497,930 A | 2/1985 | Yamasaki et al. |
| 4,605,401 A | 8/1986 | Chemilir et al. |
| 4,624,868 A | 11/1986 | Muller |
| 4,693,713 A | 9/1987 | Chmelir |
| 4,952,550 A | 8/1990 | Wallach et al. |
| 4,959,341 A | 9/1990 | Wallach |
| 4,966,694 A | 10/1990 | Namikoshi et al. |
| 5,231,122 A | 7/1993 | Palumbo et al. |
| 5,384,179 A | 1/1995 | Roe et al. |
| 5,425,725 A | 6/1995 | Tanzer et al. |
| 5,470,964 A | 11/1995 | Qin |
| 5,498,705 A | 3/1996 | Oin |
| 5,550,189 A | 8/1996 | Qin et al. |
| 5,612,411 A | 3/1997 | Gross |
| 5,688,776 A | 11/1997 | Bauer et al. |
| 5,736,595 A | 4/1998 | Gunther et al. |
| 5,801,116 A * | 9/1998 | Cottrell et al. ................. 502/404 |
| 5,847,031 A | 12/1998 | Klimmek et al. |
| 6,051,317 A | 4/2000 | Brueggemann et al. |
| 6,162,541 A | 12/2000 | Chou et al. |
| 6,288,158 B1 | 9/2001 | Schapowalov et al. |
| 6,296,936 B1 | 10/2001 | Yahiaoui et al. |
| 6,331,619 B1 | 12/2001 | Besemer et al. |
| 6,339,039 B1 | 1/2002 | Porath et al. |
| 6,387,978 B2 | 5/2002 | Ronan et al. |
| 6,436,508 B1 | 8/2002 | Ciammaichella et al. |
| 6,524,348 B1 | 2/2003 | Jewell et al. |
| 6,562,743 B1 | 5/2003 | Cook et al. |
| 6,689,934 B2 | 2/2004 | Dodge, II et al. |
| 6,713,460 B2 | 3/2004 | Huppe |
| 6,730,722 B1 | 5/2004 | Eck et al. |
| 6,765,042 B1 | 7/2004 | Thornton et al. |
| 6,846,924 B1 | 1/2005 | Malmgren et al. |
| 6,998,367 B2 * | 2/2006 | Qin ............................... 502/400 |
| 7,153,904 B2 | 12/2006 | Richardson et al. |
| 7,186,701 B2 * | 3/2007 | Kubota et al. .................. 514/54 |
| 7,306,039 B2 | 12/2007 | Wang et al. |
| 7,321,007 B2 | 1/2008 | Gagliardi et al. |
| 7,407,912 B2 | 8/2008 | Mertens et al. |
| 7,615,579 B2 | 11/2009 | Joy et al. |
| 2002/0022812 A1 | 2/2002 | Kasai et al. |
| 2003/0027787 A1 | 2/2003 | Couture |
| 2003/0068944 A1 | 4/2003 | Carlucci et al. |
| 2003/0144642 A1 | 7/2003 | Dopps et al. |
| 2003/0232965 A1 | 12/2003 | Bergeron |
| 2004/0024092 A1 | 2/2004 | Sorens et al. |
| 2004/0157734 A1 | 8/2004 | Mertens et al. |
| 2004/0214499 A1 | 10/2004 | Qin et al. |
| 2004/0236260 A1 | 11/2004 | Griffiths et al. |
| 2005/0153123 A1 | 7/2005 | Herfeft et al. |
| 2005/0155491 A1 | 7/2005 | Faust et al. |
| 2005/0214541 A1 | 9/2005 | Berrada et al. |
| 2006/0142477 A1 | 6/2006 | Glasser |
| 2006/0147689 A1 | 7/2006 | Wallajapet et al. |
| 2006/0165762 A1 | 7/2006 | Plaut et al. |
| 2007/0093907 A1 | 4/2007 | Goupil et al. |
| 2007/0141338 A1 * | 6/2007 | Ishizaki et al. ................. 428/402 |
| 2007/0179291 A1 | 8/2007 | Thibodeau et al. |
| 2008/0009616 A1 | 1/2008 | Frank et al. |
| 2008/0078514 A1 | 4/2008 | Weerawarna et al. |
| 2008/0078515 A1 | 4/2008 | Weerawarna et al. |
| 2008/0079187 A1 | 4/2008 | Weerawarna et al. |
| 2008/0079188 A1 | 4/2008 | Weerawarna et al. |
| 2008/0081165 A1 | 4/2008 | Weerawarna et al. |
| 2008/0081189 A1 | 4/2008 | Weerawarna et al. |
| 2008/0081190 A1 | 4/2008 | Weerawarna et al. |
| 2008/0081191 A1 | 4/2008 | Weerawarna et al. |
| 2008/0081843 A1 | 4/2008 | Weerawarna et al. |
| 2008/0082064 A1 | 4/2008 | Luo et al. |
| 2008/0082065 A1 | 4/2008 | Weerawarna et al. |

(Continued)

FOREIGN PATENT DOCUMENTS

| | | |
|---|---|---|
| WO | WO 00/21581 | 4/2000 |
| WO | 0170287 A2 | 9/2001 |
| WO | 2004085481 A1 | 10/2004 |
| WO | WO 2005/123781 | 12/2005 |
| WO | 2006/079221 A1 | 8/2006 |
| WO | WO 2006/079221 | 8/2006 |
| WO | 2006/119638 A1 | 11/2006 |
| WO | WO 2006/119638 | 11/2006 |

OTHER PUBLICATIONS

Final Office Action, Notification Date Apr. 5, 2011, U.S. Appl. No. 12/165,075, filed Jun. 30, 2008, First Named Inventor: S. Ananda Weerawarna.

*Primary Examiner* — Edward Johnson
(74) *Attorney, Agent, or Firm* — John M. Crawford

(57) ABSTRACT

Particles comprising a combination of a carboxyalkyl cellulose and a starch, wherein the particles comprise a plurality of non-permanent metal crosslinks. The non-permanent intra-fiber metal crosslinks include multi-valent metal ion crosslinks formed with one or more metal ions selected from aluminum, boron, bismuth, titanium, and zirconium ions.

12 Claims, No Drawings

U.S. PATENT DOCUMENTS

| | | |
|---|---|---|
| 2008/0082066 A1 | 4/2008 | Luo et al. |
| 2008/0082067 A1 | 4/2008 | Weerawarna et al. |
| 2008/0082069 A1 | 4/2008 | Qin et al. |
| 2008/0147032 A1 | 6/2008 | Luo |
| 2008/0314537 A1 | 12/2008 | Weerawarna et al. |
| 2009/0321029 A1 | 12/2009 | Weerawarna |
| 2009/0321030 A1 | 12/2009 | Weerawarna |
| 2009/0325799 A1 | 12/2009 | Weerawarna |
| 2009/0325800 A1 | 12/2009 | Weerawarna |

* cited by examiner

BIODEGRADABLE SUPERABSORBENT PARTICLES

BACKGROUND OF THE INVENTION

Personal care absorbent products, such as infant diapers, adult incontinent pads, and feminine care products, typically contain an absorbent core that includes superabsorbent polymer particles distributed within a fibrous matrix. Superabsorbents are water-swellable, generally water-insoluble absorbent materials having a high absorbent capacity for body fluids. Superabsorbent polymers (SAPs) in common use are mostly derived from acrylic acid, which is itself derived from petroleum oil, a non-renewable raw material. Acrylic acid polymers and SAPs are generally recognized as not being biodegradable. Despite their wide use, some segments of the absorbent products market are concerned about the use of non-renewable petroleum oil-derived materials and their non-biodegradable nature. Acrylic acid based polymers also comprise a meaningful portion of the cost structure of diapers and incontinent pads. Users of SAP are interested in lower cost SAPs. The high cost derives in part from the cost structure for the manufacture of acrylic acid which, in turn, depends upon the fluctuating price of petroleum oil. Also, when diapers are discarded after use they normally contain considerably less than their maximum or theoretical content of body fluids. In other words, in terms of their fluid holding capacity, they are "over-designed". This "over-design" constitutes an inefficiency in the use of SAP. The inefficiency results in part from the fact that SAPs are designed to have high gel strength (as demonstrated by high absorbency under load or AUL). The high gel strength (upon swelling) of currently used SAP particles helps them to retain a lot of void space between particles, which is helpful for rapid fluid uptake. However, this high "void volume" simultaneously results in there being a lot of interstitial (between particle) liquid in the product in the saturated state. When there is a lot of interstitial liquid the "rewet" value or "wet feeling" of an absorbent product is compromised.

In personal care absorbent products, U.S. southern pine fluff pulp is commonly used in combination with the SAP. This fluff is recognized worldwide as the preferred fiber for absorbent products. The preference is based on the fluff pulp's advantageous high fiber length (about 2.8 mm) and its relative ease of processing from a wetland pulp sheet to an airlaid web. Fluff pulp is also made from renewable and biodegradable cellulose pulp fibers. Compared to SAP, these fibers are inexpensive on a per mass basis, but tend to be more expensive on a per unit of liquid held basis. These fluff pulp fibers mostly absorb within the interstices between fibers. For this reason, a fibrous matrix readily releases acquired liquid on application of pressure. The tendency to release acquired liquid can result in significant skin wetness during use of an absorbent product that includes a core formed exclusively from cellulosic fibers. Such products also tend to leak acquired liquid because liquid is not effectively retained in such a fibrous absorbent core.

Superabsorbent produced in fiber form has a distinct advantage over particle forms in some applications. Such superabsorbent fiber can be made into a pad form without added non-superabsorbent fiber. Such pads will also be less bulky due to elimination or reduction of the non superabsorbent fiber used. Liquid acquisition will be more uniform compared to a fiber pad with shifting superabsorbent particles.

A need therefore exists for a fibrous superabsorbent material that is simultaneously made from a biodegradable renewable resource like cellulose that is inexpensive. In this way, the superabsorbent material can be used in absorbent product designs that are efficient. These and other objectives are accomplished by the invention set forth below.

SUMMARY OF THE INVENTION

The invention provides superabsorbent particles that include carboxyalkyl cellulose. The particles include a combination of a carboxyalkyl cellulose and a starch, and a plurality of non-permanent metal crosslinks.

DETAILED DESCRIPTION OF THE INVENTION

In one aspect, the present invention provides superabsorbent particles that contain carboxyalkyl cellulose. The particles include a combination of a carboxyalkyl cellulose and a starch, and a plurality of non-permanent metal crosslinks.

The particles include a carboxyalkyl cellulose. Suitable carboxyalkyl celluloses have a degree of carboxyl group substitution of from about 0.3 to about 2.5, and in one embodiment have a degree of carboxyl group substitution of from about 0.5 to about 1.5. In one embodiment, the carboxyalkyl cellulose is carboxymethyl cellulose. The particles include from about 60 to about 99% by weight carboxyalkyl cellulose based on the total weight of carboxyalkyl cellulose and starch. In one embodiment, the particles include from about 80 to about 95% by weight carboxyalkyl cellulose based on the total weight of carboxyalkyl cellulose and starch. Suitable carboxyalkyl celluloses include carboxyalkyl celluloses (carboxymethyl cellulose) obtained from commercial sources.

In addition to a carboxyalkyl cellulose, the particles of the invention include a starch. Starches are composed of two polysaccharides: amylose and amylopectin. Amylose is a linear polysaccharide having an average molecular weight of about 250,000 g/mole. Amylopectin is a branched polysaccharide (branching via 1,6-α-glucosidic links) having an average molecular weight of about 75,000,000 g/mole. Typically, the ratio of amylose to amylopectin is from about 1:4 to about 1:5.

Starches suitable for use in the present invention may be obtained from corn, wheat, maize, rice, sorghum, potato, cassava, barley, buckwheat, millet, oat, arrowroot, beans, peas, rye, tapioca, sago, and amaranth. Also suitable are waxy starches, such as from corn, wheat, maize, rice, sorghum, potato, cassava, and barley. Mixtures of starches can also be used.

Suitable starches for use in the invention include cooked and pre-gelatinized starches. Certain cooked and pre-gelatinized starches are commercially available from a variety of commercial sources.

In one embodiment, the starch is first cooked in water (e.g., 75° C. for 45 min). Then, an aqueous solution of a carboxyalkyl cellulose is added to the aqueous starch. A first crosslinking agent is added and mixed to obtain a crosslinked gel (e.g., intermolecular crosslinking of water-soluble polymers).

Starch is present in the particles in an amount from about 1 to about 20% by weight based on the weight of the particles. In one embodiment, starch is present in an amount from about 1 to about 15% by weight based on the weight of the particles. In one embodiment, starch is present in an amount from about 2 to about 15% by weight based on the weight of the particles. In certain embodiments, starch is present in an amount from about 4 to about 8% by weight based on the weight of the particles.

The particles are substantially insoluble in water while being capable of absorbing water. The particles are rendered water insoluble by a plurality of non-permanent interpolymer metal crosslinks.

The particles have intermolecular metal crosslinks between polymer molecules. The metal crosslink arises as a consequence of an associative interaction (e.g., bonding) between functional groups on the polymers (e.g., carboxy, carboxylate, or hydroxyl groups) and a multi-valent metal species. Suitable multi-valent metal species include metal ions having a valency of three or greater and that are capable of forming an associative interaction with a polymer (e.g., reactive toward associative interaction with the polymer's carboxy, carboxylate, or hydroxyl groups). The polymers are intermolecularly crosslinked when the multi-valent metal species forms an associative interaction with functional groups on two or more polymer molecules. A crosslink may be formed within one polymer molecule or may be formed between two or more polymer molecules. The extent of crosslinking affects the water solubility of the particles and the ability of the particles to swell on contact with an aqueous liquid.

The particles include non-permanent metal crosslinks formed both intermolecularly and intramolecularly in the population of polymer molecules. As used herein, the term "non-permanent crosslink" refers to the metal crosslink formed with two or more functional groups of a polymer molecule (intramolecularly) or formed with two or more functional groups of two or more polymer molecules (intermolecularly). It will be appreciated that the process of dissociating and re-associating (breaking and reforming crosslinks) the multi-valent metal ion and polymer molecules is dynamic and also occurs during liquid acquisition. During water acquisition the individual particles swell and change to gel state. The ability of non-permanent metal crosslinks to dissociate and associate under water acquisition imparts greater freedom to the gels to expand than if it was restrictively crosslinked by permanent crosslinks that do not have the ability to dissociate and reassociate. Covalent organic crosslinks such as ether crosslinks are permanent crosslinks that do not have the ability to dissociate and reassociate.

The crosslinks are formed by treating the carboxyalkyl cellulose and starch with a crosslinking agent. Suitable crosslinking agents include crosslinking agents that are reactive towards hydroxyl groups and carboxyl groups. Representative crosslinking agents include metallic crosslinking agents, such as aluminum (III) compounds, titanium (IV) compounds, bismuth (III) compounds, boron (III) compounds, and zirconium (IV) compounds. The numerals in parentheses in the preceding list of metallic crosslinking agents refers to the valency of the metal.

Representative metallic crosslinking agents include aluminum sulfate; aluminum hydroxide; dihydroxy aluminum acetate (stabilized with boric acid); other aluminum salts of carboxylic acids and inorganic acids; other aluminum complexes, such as Ultrion 8186 from Nalco Company (aluminum chloride hydroxide); boric acid; sodium metaborate; ammonium zirconium carbonate (AZC); zirconium compounds containing inorganic ions or organic ions or neutral ligands; bismuth ammonium citrate (BAC); other bismuth salts of carboxylic acids and inorganic acids; titanium (IV) compounds, such as titanium (IV) bis(triethylaminato) bis (isopropoxide) (commercially available from the Dupont Company under the designation Tyzor TE); and other titanates with alkoxide or carboxylate ligands.

The crosslinking agent is effective for intermolecularly crosslinking the carboxyalkyl cellulose (with or without carboxyalkyl hemicellulose) and starch molecules. The crosslinking agent is applied in an amount of from about 0.1 to about 20% by weight based on the total weight of the carboxyalkyl cellulose and starch. The amount of crosslinking agent applied to the polymers will vary depending on the crosslinking agent. In general, the particles have an aluminum content of about 0.04 to about 2.0% by weight based on the weight of the particles for aluminum crosslinked particles, a titanium content of about 0.1 to about 4.5% by weight based on the weight of the particles for titanium crosslinked particles, a zirconium content of about 0.09 to about 6.0% by weight based on the weight of the particles for zirconium crosslinked particles; and a bismuth content of about 0.09 to about 5.0% by weight based on the weight of the particles for bismuth crosslinked particles.

The particles are highly absorptive. The particles have a Free Swell Capacity of from about 30 to about 60 g/g (0.9% saline solution) and a Centrifuge Retention Capacity (CRC) of from about 15 to about 40 g/g (0.9% saline solution).

The particles are water insoluble and water swellable. Water insolubility is imparted by intermolecular crosslinking of the polymer molecules, and water swellability is imparted to the absorbent particles by the presence of carboxylate anions with associated cations. The particles are characterized as having a relatively high liquid absorbent capacity for water (e.g., pure water or aqueous solutions, such as salt solutions or biological solutions such as urine).

The particles are useful as a superabsorbent composition in personal care absorbent products (e.g., infant diapers, feminine care products and adult incontinence products). The particles are useful in a variety of other applications, including, for example, wound dressings, cable wrap, absorbent sheets or bags, and packaging materials.

The preparations of representative superabsorbent particles are described in Examples 1-4. In these examples, gels of a representative carboxyalkyl cellulose and starch are crosslinked with a metallic crosslinking agent. The composition and liquid absorbent characteristics of representative superabsorbent particles (flakes) are summarized in Table 1. In Table 1, "DS" refers to the carboxymethyl cellulose (CMC) degree of substitution and viscosity (cps) refers to Brookfield viscosity determined with spindle #3 at 20 rpm at 25° C. The percentages of the CMC and starch refer to the percent by weight of each component based on the total weight of the product. In Table 1, "% wgt total wgt, applied" refers to the amount of crosslinking agent applied to the total weight of CMC and starch.

The superabsorbent particles containing carboxyalkyl cellulose can be made by a method that includes the steps of (a) blending a carboxyalkyl cellulose and a starch in water to provide an aqueous gel; (b) treating the aqueous gel with a first crosslinking agent to provide a crosslinked gel; (c) drying the crosslinked gel to provide a solid; and (d) comminuting the solid to provide a plurality of particles.

In the process, a carboxyalkyl cellulose and a starch are blended in water to provide an aqueous gel. In one embodiment, the carboxyalkyl cellulose is carboxymethyl cellulose. The aqueous gel includes from about 60 to about 99% by weight carboxyalkyl cellulose based on the weight of carboxyalkyl cellulose and starch. In one embodiment, the aqueous gel includes from about 80 to about 95% by weight carboxyalkyl cellulose based on the weight of carboxyalkyl cellulose and starch.

The aqueous gel also includes a starch. The aqueous gel includes from about 1 to about 20% by weight starch based on the weight of the carboxyalkyl cellulose and starch, and in one embodiment, the aqueous gel includes from about 1 to about 15% by weight starch based on the weight of the carboxyalkyl cellulose and starch.

In the method, the aqueous gel including the carboxyalkyl cellulose and starch is treated with a crosslinking agent to provide a crosslinked gel. Suitable crosslinking agents are described above. The crosslinking agent is applied in an amount of from about 0.1 to about 20% by weight based on the total weight of the carboxyalkyl cellulose and starch. The amount of crosslinking agent applied to the polymers will vary depending on the crosslinking agent.

The crosslinked gel formed by treating the aqueous get of a carboxyalkyl cellulose and a starch with the crosslinking agent is then dried to provide a solid that is then comminuted to provide a plurality of particles (superabsorbent particles). In one embodiment, the particles are sieved to obtain particles having a size of from about 150 to about 800 μm. In one embodiment, the particles have a size less than about 1500 μm.

Test Methods

Free Swell and Centrifuge Retention Capacities

The materials, procedure, and calculations to determine free swell capacity (g/g) and centrifuge retention capacity (CRC) (g/g) were as follows.

Test Materials:

Japanese pre-made empty tea bags (available from Drugstore.com, IN PURSUIT OF TEA polyester tea bags 93 mm×70 mm with fold-over flap. (http:www.mesh.ne.jp/tokiwa/).

Balance (4 decimal place accuracy, 0.0001 g for air-dried superabsorbent polymer (ADS SAP) and tea bag weights); timer; 1% saline; drip rack with clips (NLM 211); and lab centrifuge (NLM 211, Spin-X spin extractor, model 776S, 3,300 RPM, 120 v).

Test Procedure:
1. Determine solids content of ADS.
2. Pre-weigh tea bags to nearest 0.0001 g and record.
3. Accurately weigh 0.2025 g±0.0025 g of test material (SAP), record and place into pre-weighed tea bag (air-dried (AD) bag weight). (ADS weight+AD bag weight=total dry weight).
4. Fold tea bag edge over closing bag.
5. Fill a container (at least 3 inches deep) with at least 2 inches with 1% saline.
6. Hold tea bag (with test sample) flat and shake to distribute test material evenly through bag.
7. Lay tea bag onto surface of saline and start timer.
8. Soak bags for specified time (e.g., 30 minutes).
9. Remove tea bags carefully, being careful not to spill any contents from bags, hang from a clip on drip rack for 3 minutes.
10. Carefully remove each bag, weigh, and record (drip weight).
11. Place tea bags onto centrifuge walls, being careful not to let them touch and careful to balance evenly around wall.
12. Lock down lid and start timer. Spin for 75 seconds.
13. Unlock lid and remove bags. Weigh each bag and record weight (centrifuge weight).

Calculations:

The tea bag material has an absorbency determined as follows:
Free Swell Capacity, factor=5.78
Centrifuge Capacity, factor=0.50
Z=Oven dry SAP wt (g)/Air dry SAP wt (g)
Free Capacity (g/g):

$$\frac{[(\text{drip wt (g)} - \text{dry bag wt (g)}) - (AD\ SAP\ \text{wt (g)})] - (\text{dry bag wt (g)} * 5.78)}{(AD\ SAP\ \text{wt (g)} * Z)}$$

Centrifuge Retention Capacity (g/g):

$$\frac{[\text{centrifuge wt (g)} - \text{dry bag wt (g)} - (AD\ SAP\ \text{wt (g)})] - (\text{dry bag wt (g)} * 0.50)}{(AD\ SAP\ \text{wt (g)} * Z)}$$

The following examples are provided for the purpose of illustrating, not limiting, the invention.

EXAMPLES

Example 1

The Preparation of Representative Superabsorbent Particles (Flakes)

Aluminum Sulfate Crosslinking

In this example, the preparation of representative superabsorbent composite particles crosslinked with aluminum sulfate is described.

Corn starch (Clinton 185®, Archer Daniel Midland, Ill.) (1.2 g) was cooked for 45 minutes at 75° C. in 47 mL deionized water. The cooked starch was then added to 903 mL deionized water in a Hobart mixer. Then, carboxymethyl cellulose (20 g OD northern pine wood pulp CMC, DS 0.86, 1% aqueous solution, Brookfield viscosity 2360 cps, spindle #3 and speed 20 rpm) was added with mixing. The aqueous polymer mixture was mixed for 60 minutes.

To the aqueous polymer mixture was added 0.4 g aluminum sulfate octadecahydrate (Sigma Aldrich, Wis.) in 50 mL deionized water. The polymer mixture was then mixed for 30 minutes to provide a crosslinked polymer gel.

The crosslinked polymer gel was then applied as a coating to two TEFLON coated baking pans (10 inch×17 inch) and dried at 65° C. in a safety oven to provide a film. The dried film was ground into particles for testing. Particles having sizes from 74 to 300 μm and from 300 to 850 μm were tested. The particles had free swell (50.4 g/g) and centrifuge retention capacity (33.9 g/g) for 0.9% saline solution.

Example 2

The Preparation of Representative Superabsorbent Particles (Flakes)

Aluminum Sulfate Crosslinking

In this example, the preparation of representative superabsorbent composite particles crosslinked with aluminum sulfate is described.

Corn starch (Clinton 185®, Archer Daniel Midland, Ill.) (2.4 g) was cooked for 45 minutes at 75° C. in 52 mL deionized water. The cooked starch was then added to 898 mL deionized water in a Hobart mixer. Then, carboxymethyl cellulose (40 g OD northern pine wood pulp CMC, DS 0.88, 1% aqueous solution, Brookfield viscosity 1670 cps, spindle #3 and speed 20 rpm) was added with mixing. The aqueous polymer mixture was mixed for 60 minutes.

To the aqueous polymer mixture was added 0.4 g aluminum sulfate octadecahydrate (Sigma Aldrich, Wis.) in 50 mL deionized water. The polymer mixture was then mixed for 30 minutes to provide a crosslinked polymer gel.

The crosslinked polymer gel was then applied as a coating to two TEFLON coated baking pans (10 inch×17 inch) and dried at 65° C. in a safety oven to provide a film. The dried film was ground into particles for testing. Particles having sizes from 74 to 300 µm and from 300 to 850 µm were tested. The particles had free swell (49.1 g/g) and centrifuge retention capacity (35.3 g/g) for 0.9% saline solution.

Example 3

The Preparation of Representative Superabsorbent Particles (Flakes)

Aluminum Sulfate Crosslinking

In this example, the preparation of representative superabsorbent composite particles crosslinked with aluminum sulfate is described.

Corn starch (Clinton 185®, Archer Daniel Midland, Ill.) (2.4 g) was cooked for 45 minutes at 75° C. in 53 mL deionized water. The cooked starch was then added to 897 mL deionized water in a Hobart mixer. Then, carboxymethyl cellulose (40 g OD northern pine wood pulp CMC, DS 0.96, 1% aqueous solution, Brookfield viscosity 1295 cps, spindle #3 and speed 20 rpm) was added with mixing. The aqueous polymer mixture was mixed for 60 minutes.

To the aqueous polymer mixture was added 0.2 g aluminum sulfate octadecahydrate (Sigma Aldrich, Wis.) in 50 mL deionized water. The polymer mixture was then mixed for 30 minutes to provide a crosslinked polymer gel.

The crosslinked polymer gel was then applied as a coating to two TEFLON coated baking pans (10 inch×17 inch) and dried at 65° C. in a safety oven to provide a film. The dried film was ground into particles for testing. Particles having sizes from 74 to 300 µm and from 300 to 850 µm were tested. The particles had free swell (50.5 g/g) and centrifuge retention capacity (33.0 g/g) for 0.9% saline solution.

Example 4

The Preparation of Representative Superabsorbent Particles (Flakes)

Aluminum Sulfate Crosslinking

In this example, the preparation of representative superabsorbent composite particles crosslinked with aluminum sulfate is described.

Corn starch (Clinton 185®, Archer Daniel Midland, Ill.) (2.4 g) was cooked for 45 minutes at 75° C. in 54 mL deionized water. The cooked starch was then added to 896 mL deionized water in a Hobart mixer. Then, carboxymethyl cellulose (40 g OD northern pine wood pulp CMC, DS 1.03, 1% aqueous solution, Brookfield viscosity 1465 cps, spindle #3 and speed 20 rpm) was added with mixing. The aqueous polymer mixture was mixed for 60 minutes.

To the aqueous polymer mixture was added 1.0 g aluminum sulfate octadecahydrate (Sigma Aldrich, Wis.) in 50 mL deionized water. The polymer mixture was then mixed for 30 minutes to provide a crosslinked polymer gel.

The crosslinked polymer gel was then applied as a coating to four TEFLON coated baking pans (10 inch×17 inch) and dried at 65° C. in a safety oven to provide a film The dried film was ground into particles for testing. Particles having sizes from 74 to 300 µm and from 300 to 850 µm were tested. The particles had free swell (41.6 g/g) and centrifuge retention capacity (28.2 g/g) for 0.9% saline solution.

TABLE 1

Superabsorbent Flakes From Crosslinked Aqueous Mixtures of CMC and Starch

| Sample | CMC (DS, viscosity, %) | Starch (wgt % total wgt) | Crosslinking agent $(Al_2(SO_4)_3)$ (wgt % total wgt, applied) | Free Swell (g/g) | CRC (g/g) |
|---|---|---|---|---|---|
| 1 | 0.86, 2360, 92.2 | 5.50 | 2.30 | 35.2 | 20.3 |
| 2 | 0.86, 2360, 93.5 | 5.60 | 0.90 | 50.4 | 33.9 |
| 3 | 0.88, 1670, 93.0 | 5.60 | 1.40 | 49.1 | 35.3 |
| 4 | 0.96, 1295, 94.1 | 5.70 | 0.20 | 50.5 | 33.0 |
| 5 | 1.07, 725, 93.7 | 5.60 | 0.70 | 51.6 | 30.7 |
| 6 | 1.03, 1465, 93.5 | 5.60 | 1.20 | 41.6 | 28.2 |
| 7 | 0.93, 1370, 94.1 | 5.70 | 0.20 | 54.1 | 39.4 |

While illustrative embodiments have been illustrated and described, it will be appreciated that various changes can be made therein without departing from the spirit and scope of the invention.

The embodiments of the invention in which an exclusive property or privilege is claimed are defined as follows:

1. Particles comprising a combination of a carboxyalkyl cellulose and a starch, wherein the particles comprise a plurality of non-permanent metal crosslinks and wherein the starch is cooked or pre-gelatinized and is selected from waxy starches or starches composed of only amylose and amylopectin.

2. The particles of claim 1, wherein the carboxyalkyl cellulose has a degree of carboxyl group substitution of from about 0.3 to about 2.5.

3. The particles of claim 1, wherein the carboxyalkyl cellulose is carboxymethyl cellulose.

4. The particles of claim 1, wherein the starch is selected from the group consisting of corn, wheat, maize, rice, sorghum, potato, cassaya, barley, buckwheat, millet, oat, arrowroot, beans, peas, rye, tapioca, sago, and amaranth starches.

5. The particles of claim 1, wherein the starch is present in an amount from about 1 to about 20 percent by weight based on the total weight of the particles.

6. The particles of claim 1, wherein the carboxyalkyl cellulose is present in an amount from about 60 to about 99 percent based on the total weight of particles.

7. The particles of claim 1, wherein the non-permanent metal crosslinks comprise multi-valent metal ion crosslinks.

8. The particles of claim 1, wherein the non-permanent metal crosslinks comprise one or more metal ions selected from the group consisting of aluminum, boron, bismuth, titanium, and zirconium, and mixtures thereof.

9. The particles of claim 1 having a free swell capacity of from about 30 to about 60 g/g for 0.9% saline solution.

10. The particles of claim 1 having a centrifuge retention capacity of from about 15 to about 40 g/g for 0.9% saline solution.

11. The particles of claim 1 having a size less than about 1500 µm.

12. The particles of claim 1 wherein the crosslinks do not include permanent crosslinks.

* * * * *